(12) United States Patent
Trieste, Jr.

(10) Patent No.: US 11,598,796 B2
(45) Date of Patent: Mar. 7, 2023

(54) SYSTEM FOR MEASURING A PARAMETER WITH AN ELECTRICAL METER

(71) Applicant: Consolidated Edison Company of New York, Inc., New York, NY (US)

(72) Inventor: Richard J. Trieste, Jr., Staten Island, NY (US)

(73) Assignee: CONSOLIDATED EDISON COMPANY OF NEW YORK, INC., New York, NY (US)

(*) Notice: Subject to any disclaimer, the term of this patent is extended or adjusted under 35 U.S.C. 154(b) by 566 days.

(21) Appl. No.: 16/653,025

(22) Filed: Oct. 15, 2019

(65) Prior Publication Data

US 2020/0182918 A1 Jun. 11, 2020

Related U.S. Application Data

(60) Provisional application No. 62/776,244, filed on Dec. 6, 2018.

(51) Int. Cl.
| | |
|---|---|
| *G01R 22/06* | (2006.01) |
| *H01R 13/66* | (2006.01) |
| *H01R 31/06* | (2006.01) |
| *G01N 33/00* | (2006.01) |
| *H01R 13/74* | (2006.01) |
| *G01K 13/00* | (2021.01) |
| *G01J 5/00* | (2022.01) |

(52) U.S. Cl.
CPC ............ *G01R 22/063* (2013.01); *G01J 5/00* (2013.01); *G01K 13/00* (2013.01); *G01N 33/004* (2013.01); *G01N 33/0047* (2013.01); *G01N 33/0063* (2013.01); *H01R 13/6683* (2013.01); *H01R 13/6691* (2013.01); *H01R 13/74* (2013.01); *H01R 31/065* (2013.01)

(58) Field of Classification Search
CPC ............ G01N 33/004; G01N 33/0047; G01N 33/0063; G01K 1/14; G01K 13/00; G01J 5/00; G01R 22/063
See application file for complete search history.

(56) References Cited

U.S. PATENT DOCUMENTS

| | | | |
|---|---|---|---|
| 3,755,125 A | 8/1973 | Shaw et al. | |
| 9,046,390 B2 | 6/2015 | Lye et al. | |
| 2004/0061623 A1* | 4/2004 | Tootoonian Mashhad | G01D 4/008 340/870.02 |

(Continued)

FOREIGN PATENT DOCUMENTS

| | | | | |
|---|---|---|---|---|
| CN | 108896801 A | * | 11/2018 | |
| EP | 3982087 A1 | * | 4/2022 | |
| GB | 2461348 A | * | 1/2010 | ............ G01D 4/004 |

*Primary Examiner* — Natalie Huls
(74) *Attorney, Agent, or Firm* — Cantor Colburn LLP

(57) ABSTRACT

A system and method for measuring a parameter level is provided. The system including an electricity meter, the meter having an electricity measurement sensor having a source side and a load side. A socket and a collar are provided. The collar being electrically connected between the socket and the electricity meter, the collar having at least one first connector for a first phase of electricity and at least one second connector for a second phase of electricity, the first connector and second connector being electrically coupled to the load side, and a sensor electrically connected to at least one of the at least one first connector and the at least one second connector.

24 Claims, 4 Drawing Sheets

(56) References Cited

U.S. PATENT DOCUMENTS

| | | | |
|---|---|---|---|
| 2004/0130459 A1* | 7/2004 | Ramirez | G01D 4/002 |
| | | | 340/870.01 |
| 2019/0120885 A1* | 4/2019 | Kraus | G01R 22/066 |
| 2019/0219618 A1* | 7/2019 | Davis | G01R 22/063 |
| 2022/0283245 A1* | 9/2022 | White | G01R 31/52 |

* cited by examiner

SYSTEM FOR MEASURING A PARAMETER WITH AN ELECTRICAL METER

CROSS REFERENCE TO RELATED APPLICATIONS

This application claims the benefit of U.S. Provisional Application Ser. No. 62/776,244, filed Dec. 6, 2018, the entire disclosure of which is incorporated herein by reference.

BACKGROUND

The present invention relates generally to a system for detecting a condition, such as but not limited to gas, smoke, or temperature, and in particular to a system that is coupled to an electric meter for powering a sensor.

The detection and measurement of gases such as combustible gases is desirable by an utility or electricity provider for early detection or prevention of an undesired condition. Gas sensors may be installed on natural gas services or building walls where meters are located within buildings in the vicinity of the gas service point of entry. These sensors are powered by a battery which is a finite supply of power governed by its having an operating life i.e. for five years. It should be appreciated that with a large volume of customers, the utility desiring gas detection by the electric meter will very quickly be spending a large number of resources at a large cost on simply changing batteries in sensors on a periodic basis.

Thus, there remains a need for improvements in gas sensors installed at end use customer buildings. In particular, there remains a need for improvements in extending the operating life of the sensor.

SUMMARY

According to an aspect of the disclosure, a system for measuring a parameter level is provided. The system including an electricity meter, the meter having an electricity measurement sensor having a source side and a load side. A socket and a collar are provided. The collar being electrically connected between the socket and the electricity meter, the collar having at least one first connector for a first phase of electricity and at least one second connector for a second phase of electricity, the first connector and second connector being electrically coupled to the load side, and a sensor electrically connected to at least one of the at least one first connector and the at least one second connector.

According to another aspect of the disclosure, a system for measuring gas is provided. The system being adapted to operably couple with an electricity meter having a first connector for a first phase of electricity and a second connector for a second phase of electricity, the first connector and second connector being electrically coupled to a source side of an electricity measurement sensor. The system includes a collar housing having a sidewall defining a hollow interior. A first phase conductor is coupled to the housing and configured to electrically couple the first connector with a meter socket. A second phase conductor is coupled to the housing and configured to electrically couple the second connector with a meter socket. A gas sensor is electrically coupled to at least one of the first phase conductor or second phase conductor, the gas sensor being at least partially disposed within the hollow interior.

According to yet another aspect of the disclosure, a method for measuring a parameter using utility electric power is provided. The method includes providing an electricity meter, the meter having a electricity sensor having a source side and a load side. A socket is provided. A collar is provided having at least one first connector for a first phase of electricity and at least one second connector for a second phase of electricity, the collar having a sensor electrically coupled to one of the first connector or the second connector. The collar is connected between the electricity meter and the socket, the first connector and second connector being electrically coupled to the source side. Electricity is provided from one of the first connector or second connector to the sensor. At least one parameter is measured with the sensor.

These and other advantages and features will become more apparent from the following description taken in conjunction with the drawings.

BRIEF DESCRIPTION OF THE DRAWINGS

Referring now to the drawings, which are meant to be exemplary and not limiting, and wherein like elements are numbered alike.

DETAILED DESCRIPTION OF THE INVENTION

Figure 1:
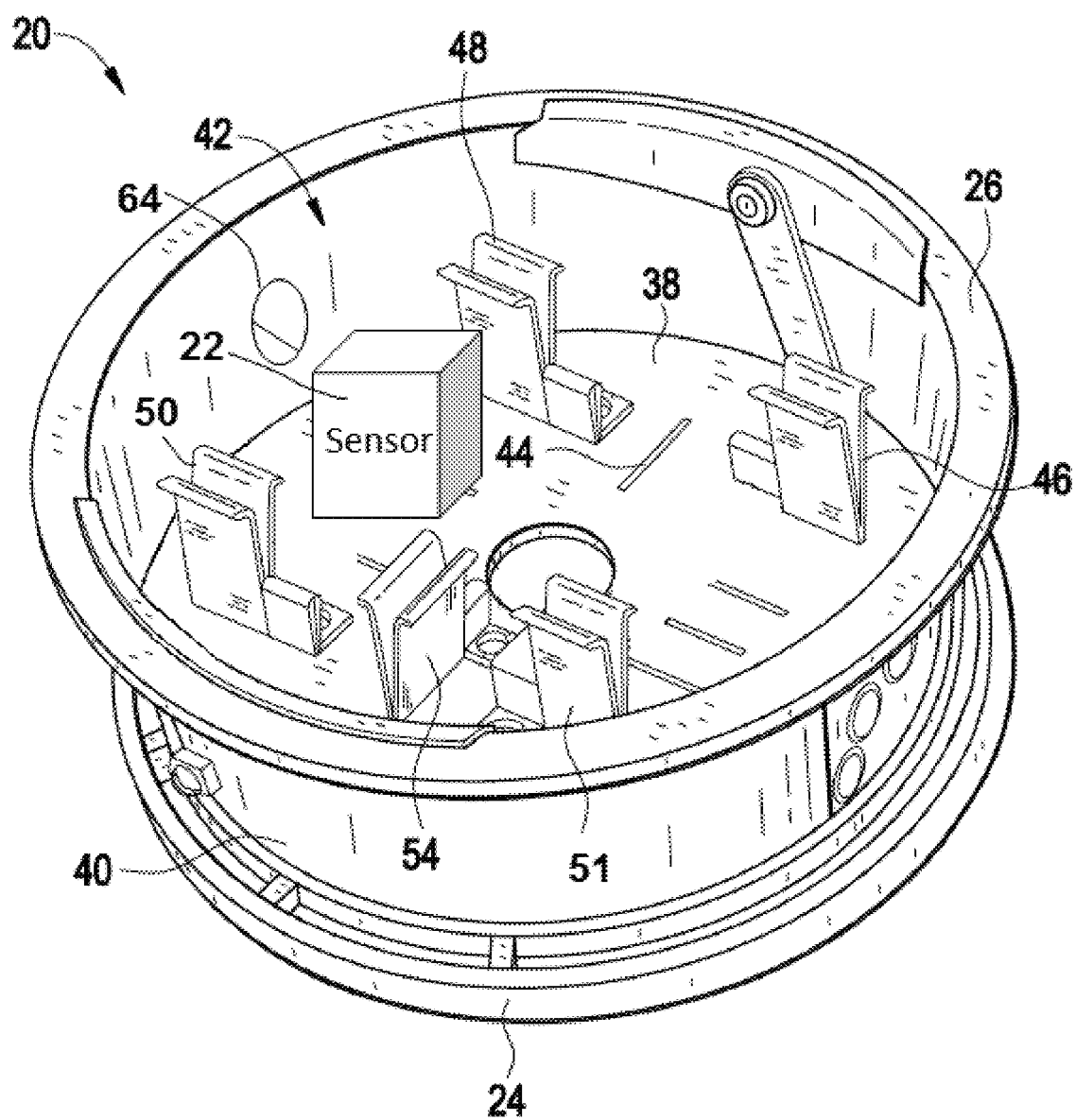
FIG. 1 is a perspective view of an electrical meter collar having a gas sensor installed therein in accordance with an embodiment.
Figure 2:
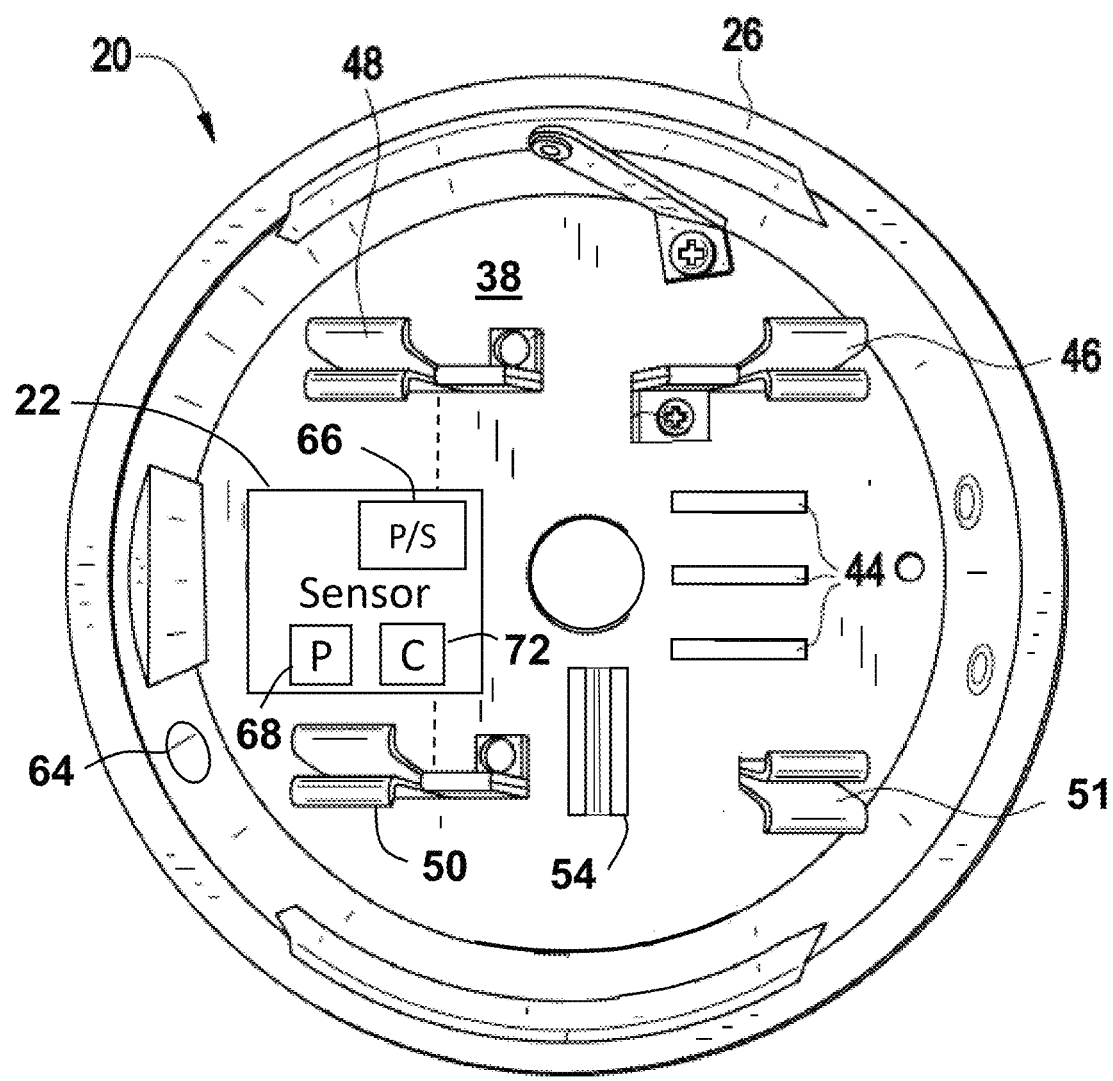
FIG. 2 is a top view of the electrical meter collar of FIG. 1.
Figure 3:
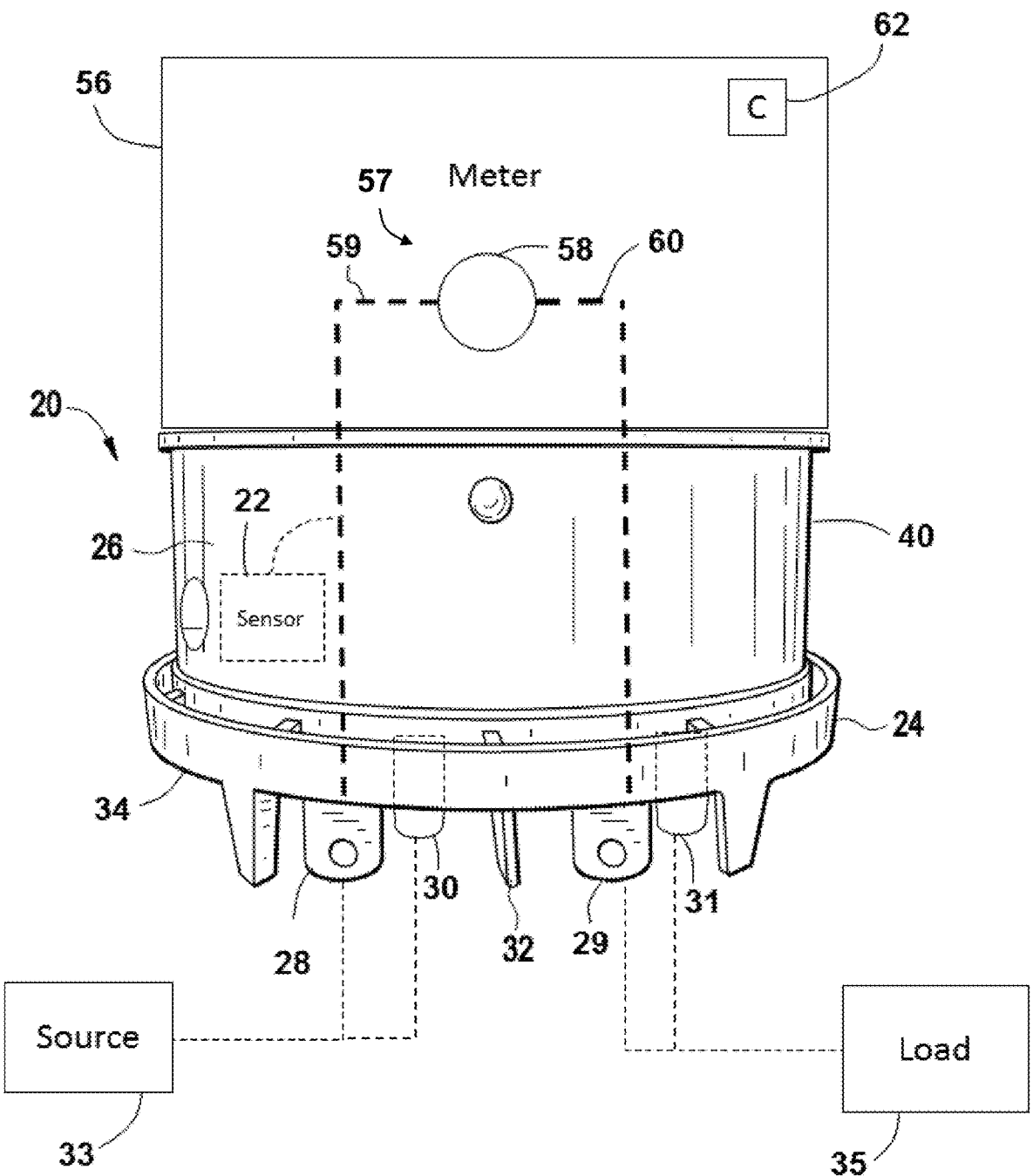
FIG. 3 is a side view of the electric meter collar coupled to an electric meter in accordance with an embodiment.

FIGS. 1-4 illustrate an electrical meter bridging adapter or collar 20 having a sensor 22 installed therein according to an embodiment for use with measuring a gas level in the atmosphere in the vicinity of the sensor 22, or the presence of a gas, typically at a residential location. The bridging adapter 20 includes a base 24 coupled to a housing 26. In another embodiment, base 24 with housing 26 and side 40 is one element. The base 24 includes a pair of first phase conductor 28, 30, a pair of second phase conductors 30, 31 and a neutral conductor 32 (FIG. 3). The conductors 28, 30 are coupled to a power source 33 (e.g. an electric utility grid) and the conductors 29, 31 are coupled to an electrical load 35 (e.g. a residential unit). The conductors 28, 29, 30, 31, 32 extend from a bottom surface 34 of the base 24. In the embodiment shown, the base 24 and conductors 28, 29, 30, 31, 32 are generally adapted to interface with a standard electrical meter socket 36 (FIG. 4), such as those used by electrical utilities on residential buildings for example.

Figure 4:
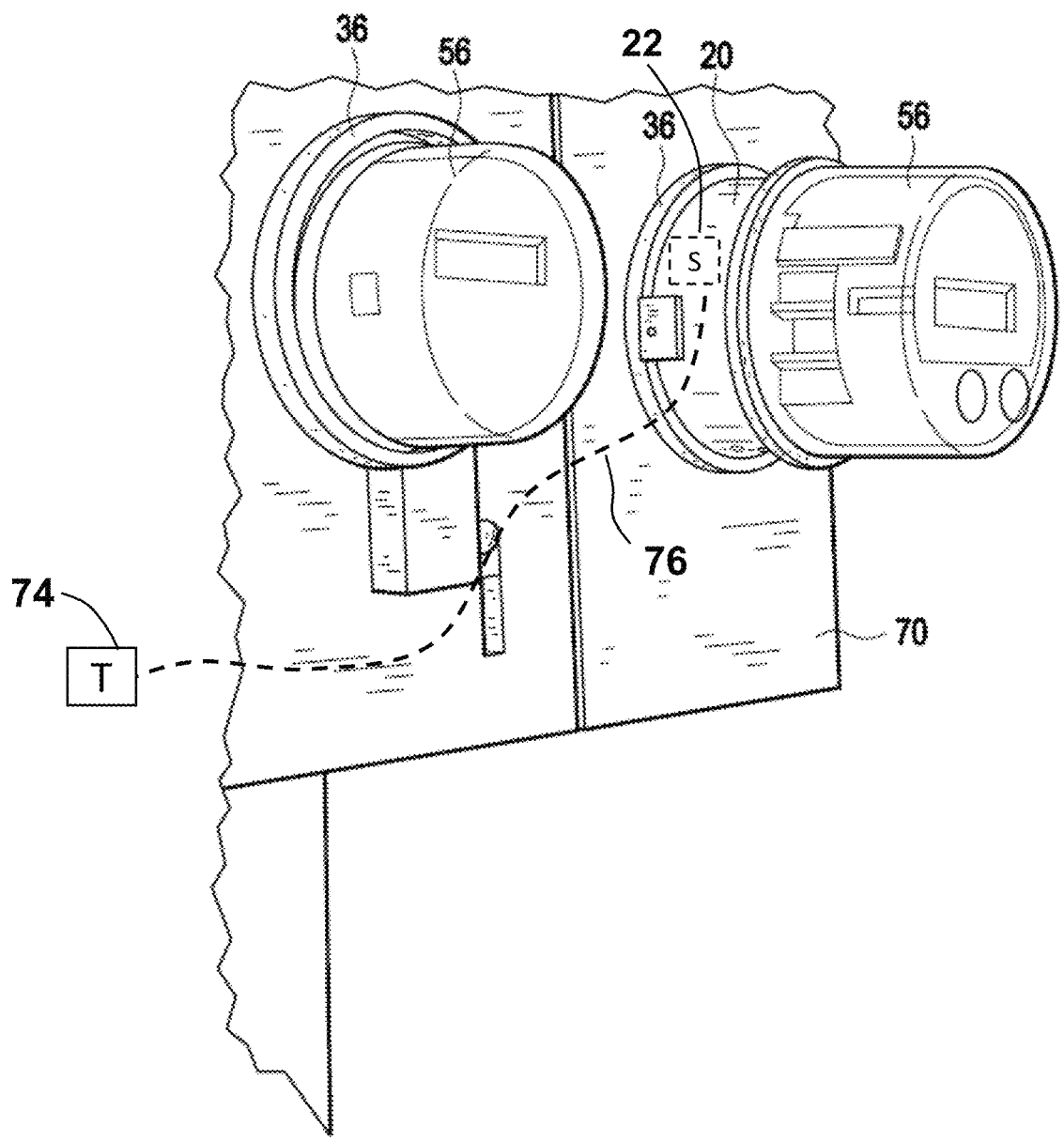
FIG. 4 is an electric meter collar coupled to an electric meter and having an external sensing element.

The housing 26 includes a generally flat bottom panel 38, and a circular side-wall 40 extending about its periphery. The panel 38 and side-wall 40 define a hollow interior portion 42 of the collar 20. A plurality of elongated openings 44 may be located in the flat panel 38. The openings 44 allow the conductors 28, 29, 30, 31, 32 extend through the openings 44 and into the interior portion 42 of the collar 20. The first phase input/source conductor 28 is coupled to a bayonet stab electrically-conductive connector 50 made from, e.g., copper. The first phase output/load conductor 29 is coupled to a bayonet stab 51. The second phase input/source conductor 31 is coupled to a bayonet stab 48 and second phase output/load conductor 31 is coupled to a bayonet stab 46. The neutral conductor 32 is coupled to a bayonet stab 54 as well. In the embodiment shown, each of the bayonet stabs 46, 48, 50, 51, 54 is adapted to interface with corresponding conductors (not shown) in an electrical meter 56 (FIG. 4).

The collar 20 is configured to couple between the socket 36 and an electrical meter 56. The electrical meter 56 includes an electricity measurement device 57, such as a current transformer 58 for example. The electricity measurement device 57 includes an input or source side 59 and an output or load side 60. The source side 59 is electrically coupled to the source phase conductors 28, 30 via the bayonet stabs 50, 48 and the load side 60 is coupled to the load phase conductors 29, 31 via the bayonet stabs 51, 46. In this way, the electricity measurement device 57 measure the amount of electrical energy used or consumed by the electrical load 35. It should be appreciated that sensor 22 is powered on the source side of the electricity measurement device 57 so the consumption of electric power by sensor 22 is not metered.

In some embodiments, electrical meters 56 include a communications circuit 62 that is configured to communicate data either through wired (e.g. power line carrier or PLC) or wireless (e.g. cellular, WiFi/IEEE 802.11, mesh networks, low power long range wireless, ZigBee or Wi-SUN) communication mediums with the electrical utility. In an embodiment, the communications network is an Advanced Metering Infrastructure (AMI) network (ANSI C12.18, IEC 61107, IEC 62056, OSGP-AES-128-PSK).

It should be appreciated that electrical meters 56 are usually located on premises, in buildings, or other facilities/units that also may utilize other utilities, such as natural gas. In an embodiment, the collar 20 includes a sensor 22, such as a natural gas sensor, a propane sensor, a combustible gas sensor, a methane sensor, a butane sensor or a combination of the foregoing for example. The sensor 22 is configured to measure a parameter that is of interest to the utility, such as the presence of a combustible gas. In one embodiment, the housing 26 includes one or more openings 64 that extend through the side-wall 40. It should be appreciated multiple openings 64 would allow the gas of interest to be accessible to sensor 22. In an embodiment, at least one opening is positioned adjacent the sensor 22. In this way, in the event that a measurable gas is present in the external environment in which the collar 20 and electrical meter 56 are located, then the sensor 22 can measure the level of the gas.

In an embodiment, the sensor 22 is electrically coupled to at least one of the source bayonet stabs 50, 46. It should be appreciated that by electrically coupling the sensor 22 prior to the measurement device, the consumption of electrical energy by the sensor 22 is not measured, and therefore not attributed or charged to the end customer. In an embodiment, the sensor 22 may include a power supply 66. The power supply 66 adapts the electrical power delivered by the power source 33 (e.g. 120V) into a form usable by the sensor 22. In an embodiment, the sensor 22 may include a control circuit or processor 68 that is configured to measure or determine the gas level and compare the measured level with one or more predetermined thresholds. In an embodiment, when the measured gas level exceeds a predetermined threshold, the processor 68 transmits a signal via a communications circuit 72. The communications circuit 72 may transmit a signal back to central location via wired or wireless communications mediums, such as the aforementioned PLC, cellular, WiFi (802.11), mesh networks, low power long range wireless, ZigBee, Wi-SUN networks or a combination of the foregoing for example. In an embodiment, the communications circuit 72 transmits the signal via an AMI network. In another embodiment, the communications circuit 72 may be coupled for communication with a communications circuit 62 of the electrical meter 56. In this embodiment, the signal may be transmitted to the communications circuit 62 and then from the electrical meter 56 to a utility central location. In an embodiment, the communications circuit 72 is integral with the sensor 22.

Referring now to FIG. 4, an embodiment of the system is shown installed at an end use location that is powered through meter pan 70 (e.g. a residential building). In an embodiment, the electrical meter 56 may be installed within an interior space of the building. In another embodiment, the electrical meters 56 may be installed on an exterior of the building that is powered through meter pan 70. To install the collar 20 with the sensor 22, a field technician removes the electrical meter 56 from the socket 36. The collar 20 is then installed on socket 36 and the electrical meter 56 is coupled to the collar 20. Once the electrical meter 56 is installed, the sensor 22 is powered and will start measuring the desired parameter.

It should be appreciated that in some embodiments, the location where gas is to be measured may not be at the same location as the electrical meter 56. For example, the socket 36 may be located on the exterior of a building that is powered through meter pan 70 in a well ventilated area. In an embodiment, the sensor 22 may include a measurement portion 74 that may be located remote or separate from the body of the sensor 22 within the interior portion 42. In an embodiment, the measurement portion 74 may be an electrochemical sensor, a metal oxide sensor, a catalytic sensor or an infrared sensor for example. In this embodiment the measurement portion 74 is positioned is a desired location (e.g. a basement or living space of the building on which the pan 70 is mounted) and is connected to the main body of the sensor 22 via either a wired or wireless communications line/medium 76.

In an embodiment, the collar 20 is configured to be compatible with 240V single phase three wire (four-jaw) service (e.g. meter form 2 s) or 120/208V single phase three wire (five-jaw) service from a three-phase transformer (e.g. meter form 12 s/25 s). In an embodiment, the neutral conductor 32 and bayonet stab 54 are only present in the 120/208V configuration.

It should be appreciated that while embodiments herein describe the sensor 22 as being a gas sensor, this is for exemplary purposes and the claims should not be so limited. In other embodiments, the sensor 22 may detect or measure other parameters of interest to the utility. Parameters may include, but are not limited to natural gas level, propane level, methane level, smoke, carbon monoxide level, infrared energy, or temperature for example.

While the invention has been described with reference to exemplary embodiments, it will be understood that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A system for measuring a parameter level of combustible gases in the atmosphere outside of the system, the system comprising:
    an electricity meter, the electricity meter having an electricity measurement sensor having a source side and a load side;
    a socket;
    a collar electrically connected between the socket and the electricity meter, the collar having at least one first connector for a first phase of electricity and at least one second connector for a second phase of electricity, the at least one first connector and the at least one second connector being electrically coupled to the load side; and
    a gas sensor electrically connected to at least one of the at least one first connector and the at least one second connector and disposed within the collar, the sensor being configured to measure the parameter level in the atmosphere outside of the collar.

2. The system of claim 1, wherein the collar further includes a housing, the sensor being at least partially disposed within the housing.

3. The system of claim 2, wherein the housing further includes an opening extending between a hollow interior and an external environment, the sensor being fluidly coupled to the atmosphere through the opening.

4. The system of claim 3, wherein the sensor includes a measurement portion.

5. The system of claim 4, wherein the measurement portion is disposed within the housing.

6. The system of claim 1, wherein the electricity meter, the socket and the collar are located at premises of a customer of an electricity provider.

7. The system of claim 1, further comprising a first communications circuit operably coupled to the sensor, the first communications circuit being operable to transmit a signal in response to the sensor measuring a parameter that exceeds a predetermined threshold.

8. The system of claim 7, wherein the first communications circuit is disposed within the collar.

9. The system of claim 8, further comprising a second communications circuit disposed within the electricity meter, the second communications circuit being coupled for communication between the first communications circuit and a utility central location.

10. The system of claim 7, wherein the first communications circuit is disposed within the electricity meter.

11. The system of claim 1, wherein the sensor is configured to measure at least one parameter, the at least one parameter being selected from a group comprising: natural gas, propane, methane, carbon monoxide, and smoke.

12. A system for measuring a parameter level, comprising:
    an electricity meter, the electricity meter having an electricity measurement sensor having a source side and a load side;
    a socket;
    a collar electrically connected between the socket and the electricity meter, the collar having at least one first connector for a first phase of electricity and at least one second connector for a second phase of electricity, the at least one first connector and the at least one second connector being electrically coupled to the load side; and
    a sensor electrically connected to at least one of the at least one first connector and the at least one second connector;
    wherein the collar further includes a housing, the sensor being at least partially disposed within the housing;
    wherein the housing further includes an opening extending between a hollow interior and an external environment;
    wherein the sensor includes a measurement portion; and
    wherein the measurement portion is disposed in the external environment.

13. A bridging adapter for measuring gas, the bridging adapter being adapted to operably couple with an electricity meter having a first connector for a first phase of electricity and a second connector for a second phase of electricity, the first connector and the second connector being electrically coupled to a source side of an electricity measurement sensor, the bridging adapter comprising:
    a collar housing having a sidewall defining a hollow interior;
    a first phase conductor coupled to the collar housing and configured to electrically couple the first connector with a meter socket;
    a second phase conductor coupled to the collar housing and configured to electrically couple the second connector with the meter socket; and
    a gas sensor electrically coupled to at least one of the first phase conductor or the second phase conductor, the gas sensor being at least partially disposed within the hollow interior, the gas sensor being fluidly coupled an external environment and configured to measure a gas level in the external environment outside of the collar housing.

14. The bridging adapter of claim 13, wherein the collar housing has at least one opening extending through the sidewall, the gas sensor being fluidly coupled to the external environment through the at least one opening.

15. The bridging adapter of claim 14, wherein the collar housing is configured to be coupled between the electricity meter and the meter socket.

16. The bridging adapter of claim 13, wherein the gas sensor includes a measurement portion.

17. The bridging adapter of claim 16, wherein the measurement portion is disposed within the hollow interior.

18. The bridging adapter of claim 13, wherein the gas sensor includes a communications circuit.

19. A bridging adapter for measuring gas, the bridging adapter being adapted to operably couple with an electricity meter having a first connector for a first phase of electricity and a second connector for a second phase of electricity, the first connector and the second connector being electrically coupled to a source side of an electricity measurement sensor, the bridging adapter comprising:
    a collar housing having a sidewall defining a hollow interior;
    a first phase conductor coupled to the collar housing and configured to electrically couple the first connector with a meter socket;
    a second phase conductor coupled to the collar housing and configured to electrically couple the second connector with the meter socket; and a gas sensor electrically coupled to at least one of the first phase conductor or the second phase conductor, the gas sensor being at least partially disposed within the hollow interior;

wherein the gas sensor includes a measurement portion; and wherein the measurement portion is disposed external to the collar housing.

20. A method for measuring a parameter using utility electric power, the method comprising:

providing an electricity meter, the electricity meter having a electricity sensor having a source side and a load side;

providing a socket;

providing a collar having at least one first connector for a first phase of electricity and at least one second connector for a second phase of electricity, the collar having a sensor electrically coupled to one of the at least one first connector or the at least one second connector;

connecting the collar between the electricity meter and the socket, the at least one first connector and the at least one second connector being electrically coupled to the source side;

providing electricity from one of the at least one first connector or the at least one second connector to the sensor;

measuring at least one parameter with the sensor; and measuring a natural gas level with the sensor in an atmosphere outside of the collar.

21. The method of claim 20, further comprising transmitting a signal with a communications circuit when the natural gas level is above a predetermined threshold.

22. The method of claim 21, wherein the communications circuit is integral with the sensor.

23. The method of claim 21, wherein the signal is transmitted via an advanced metering infrastructure (AMI) network.

24. The method of claim 20, wherein the electricity meter, the socket and the collar are located at premises of a customer of an electricity provider.

* * * * *